United States Patent [19]
Kuzmak

[11] Patent Number: 5,522,788
[45] Date of Patent: Jun. 4, 1996

[54] FINGER-LIKE LAPAROSCOPIC BLUNT DISSECTOR DEVICE

[76] Inventor: Lubomyr I. Kuzmak, 30 Crest Dr., South Orange, N.J. 07079

[21] Appl. No.: 329,453

[22] Filed: Oct. 26, 1994

[51] Int. Cl.⁶ .................................................. A61B 1/00
[52] U.S. Cl. ........................... 600/141; 128/751; 606/190
[58] Field of Search ..................... 600/139, 141, 600/142, 146, 149, 183, 201, 204, 206, 209, 216, 137; 606/205, 190; 128/751

[56] References Cited

U.S. PATENT DOCUMENTS

| | | |
|---|---|---|
| 3,730,185 | 5/1973 | Cook et al. . |
| 4,271,845 | 6/1981 | Chikashige et al. . |
| 4,762,120 | 8/1988 | Hussein ............................... 600/137 X |
| 4,807,626 | 2/1989 | McGirr . |
| 4,911,148 | 3/1990 | Sosnowski et al. ....................... 128/6 |
| 4,998,527 | 3/1991 | Meyer . |
| 5,195,968 | 3/1993 | Lundquist et al. . |
| 5,201,752 | 4/1993 | Brown et al. ............................. 606/190 |
| 5,211,655 | 5/1993 | Hasson ................................... 128/751 X |
| 5,284,128 | 2/1994 | Hart . |

*Primary Examiner*—Richard J. Apley
*Assistant Examiner*—Beverly M. Flanagan
*Attorney, Agent, or Firm*—Larson and Taylor

[57] ABSTRACT

A blunt laparoscopic dissector device is provided which includes an elongate dissector element including a "finger-like" flexible distal end portion. A cylinder or barrel member disposed at one end of a pair of pivotable control arms provides rotatable mounting of the dissector element. A control assembly, including a control rod connected to the other control arm and extending along the length of dissector element, exerts a force on the dissector element so as to produce the desired curvature of the flexible distal end portion. A locking mechanism maintains the force on the dissector element so as to maintain the desired curvature. Rotation of the dissector element within the cylinder enables a surgeon to effect control of the movement of the tip thereof while holding the device in a comfortable stationary position.

22 Claims, 2 Drawing Sheets

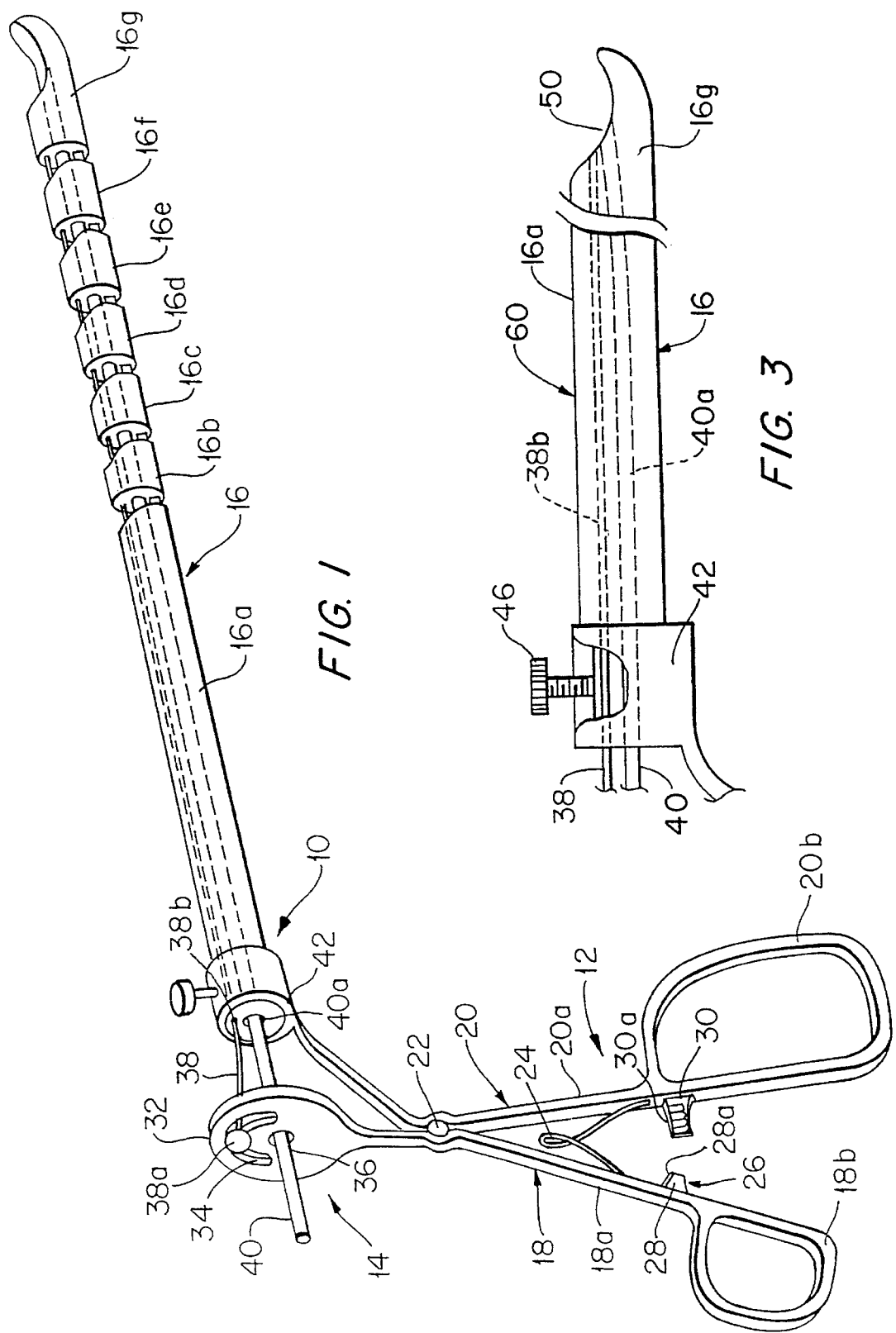

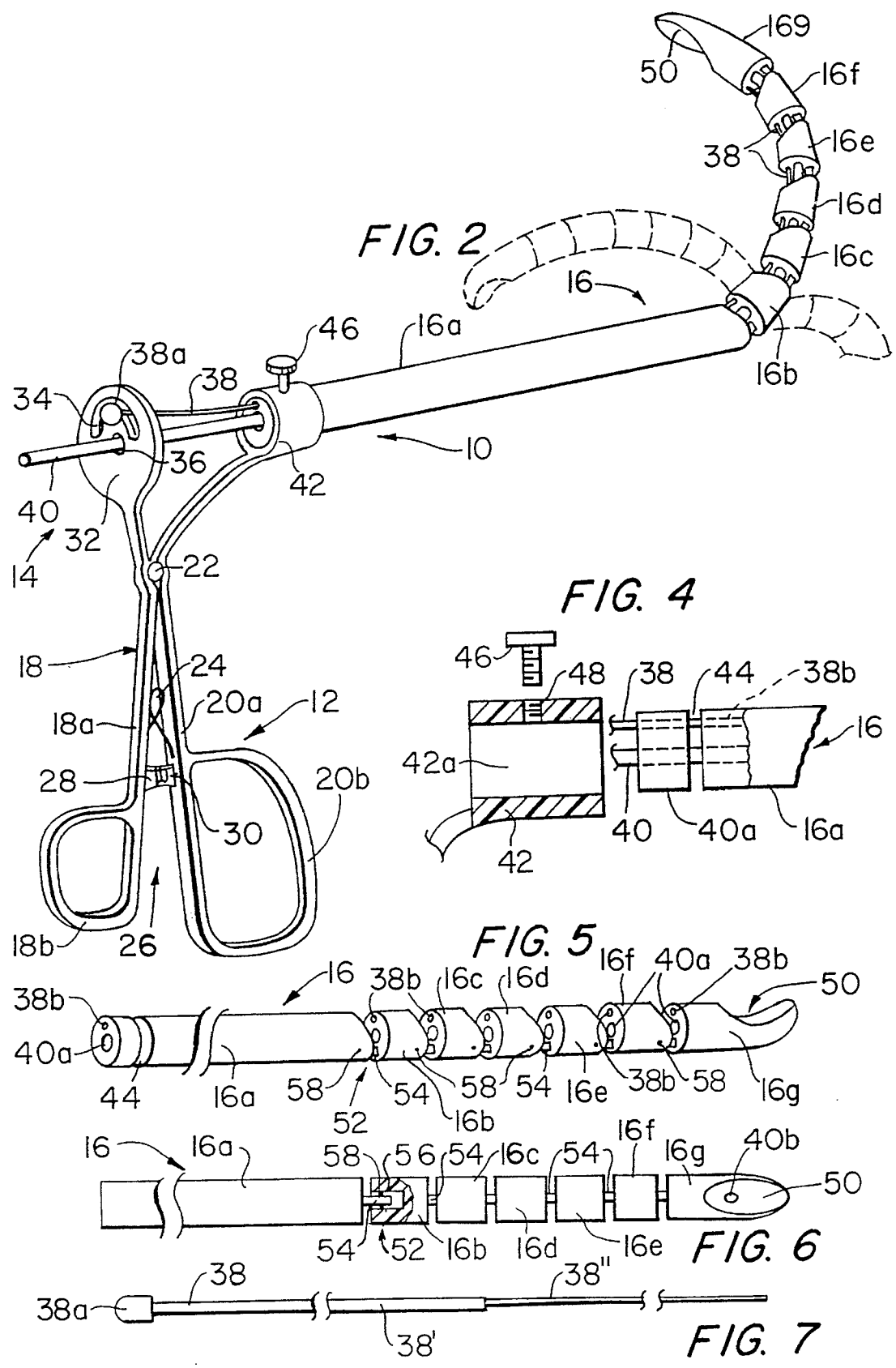

FINGER-LIKE LAPAROSCOPIC BLUNT DISSECTOR DEVICE

FIELD OF THE INVENTION

The present invention relates to dissector devices for use in surgical procedures and, more particularly, to an improved blunt dissector device which is particularly adapted for use in laparoscopic surgery.

BACKGROUND OF THE INVENTION

Most laparoscopic and open surgical procedures require some "blunt" anatomical dissection to, for example, separate the tissue and hold the tissue out of the way of the operating site. In laparoscopic surgery, dissection is done most commonly with electrical cautery or, in some procedures, using thin mechanical dissectors, sometimes combined with cauterization. Both of these approaches present the possibility of perforation of the dissected organ.

A number of different mechanical dissectors have been used in surgical procedures. Patents of interest or possible interest in the broad field of medical manipulators and in other medical fields include the following: U.S. Pat. Nos. 5,284,128 (Hart); 5,195,968 (Lundquist et al.); 4,998,527 (Meyer); 4,807,626 (McGirr); 4,271,845 (Chikashige et al.); and 3,730,185 (Cooke et al.).

The Hart patent discloses a surgical manipulator having a long outer tube with a distal end and a proximal end. The proximal end is connected to a handle. The distal end is constructed so that one sidewall of the outer tube is relatively weak compared to the opposite sidewall. An inner tube, smaller in diameter than the outer tube, is positioned longitudinally within the outer tube and the distal ends of the inner and outer tubes are connected together while the proximal end of the inner tube is connected to a finger tab that is slidably located on the handle. When the finger tab is slid forward or backward in relation to the handle, the tab creates a compression or tension in the inner tube. The inner tube translates that force to the outer tube at the distal connection, and in response to that force, the outer tube curls in one direction, either toward or away from the weaker wall, depending on whether the force is compression or tension. Thus, the end of the outer tube (as well as the inner tube encased within) can be made to curl in either of two directions. The patent discloses that the inner element could be in the form of a wire rather than a tube. By using a tube as the inner element, however, the device allows the insertion of other laparoscopic devices through the inner opening as well as allowing suction of fluid from the body cavity back through the opening.

The Lundquist et al patent discloses a steering mechanism for use with a catheter. The mechanism includes a hollow tube with a proximal end connected to a handle and a flexible distal end having a flat lead spring mounted therewithin. The lead spring serves to provide memory for the distal end so that the distal end reverts to its straightened position when not under tension. Longitudinally positioned within the hollow tube is a steering wire that is connected to the lead spring at its distal end and to one of several tension producing mechanisms at its proximal end in the handle. When tension is placed on the steering wire the distal end of the tube curls in the direction of the side of the spring to which the wire is connected. In another embodiment, two steering wires can be used so that the tube can be forced to curl in either of two opposite directions. Because the device is designed only to steer a catheter, it is not adapted to carry other instruments or to allow fluid flow within the tube.

The Chikashige et al. patent discloses a device for guiding a medical instrument by bending a shaft that holds the end of the instrument. The outer shaft is a cylindrical coil or spring. The distal end of the coil is coarsely wound and has one sidewall weaker than its opposing sidewall. The different sidewall strengths can be accomplished through a number of illustrated methods. A wire is longitudinally positioned through the center of the spring and connected to the distal end of the spring. Tension placed on the wire causes the distal end of the spring to curl in a direction away from the weaker sidewall, thus guiding the medical instrument that is attached to the distal end of the spring. The patent also provides for a control wire to be longitudinally positioned within the spring for operating instruments such as forceps that may be attached to the distal end of the spring.

The McGirr patent discloses a stone extractor for use within body cavities which includes a tube with a distal end connected to a self-closing basket and a control wire longitudinally positioned within the tube for opening the basket. The patent provides that fluids can flow through the interior of the tube. In one embodiment, the tube is made from a flexible material that has elastic memory and is formed with a predetermined curvature. A rigid sleeve is slid over the tube to keep it straight as the tube is inserted through an endoscope and the sleeve is retraced to allow the tube to resume its pre-formed curl once inside the cavity. In this manner the basket is guided to its desired location.

The Meyer patent discloses an endoscope tissue removing device performing multiple functions necessary for viewing and resecting tissue. The distal end of an inner tube is rotated in relation to an outer tube to aid in resecting the tissue.

The Cooke et al. patent discloses a method of removing arteriosclerotic material from an artery. The distal end of a rod is formed into a loop and is oscillated to cause a separation of the material from the artery.

SUMMARY OF THE INVENTION

According to the invention, a blunt dissector device is provided which overcomes or reduces the dangers and disadvantages associated with prior art dissectors and also provides positive advantages.

In accordance with one preferred embodiment of the invention, a blunt dissector device is provided which comprises: an elongate dissector element including a movable flexible distal end portion; control means connected to the dissector element for controlling movement of the flexible distal end portion so as to control the curvature (bending or curling) thereof; and mounting means for rotatably mounting the proximal end portion of the dissector element so as to enable the dissector element to be rotated relative to the mounting means so as to control positioning of the tip of the dissector element. The latter feature enables the overall device to be held in a comfortable position while still permitting the tip to be moved to a desired position or site.

Preferably, the control means includes locking means for maintaining the desired curvature of said flexible distal end portion.

In a particularly advantageous implementation, the control means includes a control rod extending along the dissector element and comprising a first relatively non-flexible proximal portion disposed with the proximal end portion of the dissector element and second, relatively flexible distal portion disposed within the distal end portion of said dissector element, the proximal end portion of the dissector element being substantially non-flexible and the control means further comprising manually operated means connected to the control rod for effecting angular rotation of the proximal end portion of the dissector element within the mounting means so as to cause rotation of dissector element without movement of the mounting means.

The control means preferably includes a pair of pivotable control arms pivotably connected together intermediate the ends thereof, one end of one of the control arms being connected to the control rod to control movement thereof and one end of the other of the control arms being connected to the mounting means. The control arms advantageously include gripping loops at the other, distal ends thereof, and, preferably, the device further comprises a spring means for biasing the gripping loops away from each other. Advantageously, one control arm includes, at the one end thereof, a plate member having a curved (preferably semicircular) slot therein defining end points and the control rod extends through the curved slot and includes said manually operated means (e.g., a control knob) at the proximal end thereof for enabling control of movement of the control rod within the slot, thereby to selectively control angular movement of the dissector element between said end points In accordance with an important feature, the dissector element further comprises a resilient outer covering or cuff made of a silicone or the like and presenting a smooth surface.

In an important implementation, the device further comprises securing means for releasably securing said dissector element in a desired angular position. Advantageously, the securing means comprising a circumferential groove in the outer surface of the dissector element at the proximal end thereof, and a set screw, disposed in the mounting means for the dissector element, for, in use, engaging in the groove to fix the angular position of the dissector element.

Preferably, the dissector element includes a non-pivotable dissector member and plurality of pivotable dissector members arranged in serial relation and hinged together to enable pivoting thereof relative to one another. In this implementation, the relatively non-flexible portion of the control rod extends through the non-pivotable dissector member and the relatively flexible portion of said control rod extends through said pivotable dissector members and is connected to the most distal pivotable dissector member.

In accordance with a further feature of the invention, a tubular member is provided which extends along the length of the dissector element and terminates at the most distal dissector member for permitting the insertion of auxiliary implements through the dissector element.

Other features and advantages of the invention will be set forth in, or apparent from, the following detailed description of preferred embodiments of the invention.

BRIEF DESCRIPTION OF THE DRAWINGS

FIG. 1 is a perspective view of a preferred embodiment of the dissector device of the invention, with the outer covering for the dissector portion or element removed;

FIG. 2 is a perspective view similar to that of FIG. 1 showing vertical flexure or bending of the distal end of the dissector element in solid lines, and showing two other possible bending positions in dashed lines;

FIG. 3 is a side elevational view, partially broken away, of the dissector element and a portion of the remainder of the device and including the outer covering;

FIG. 4 is a an exploded cross section view of the components shown in FIG. 3;

FIG. 5 is a perspective view of the dissector element of FIG. 1, with parts removed;

FIG. 6 is a top plan view, partially broken away, of the dissector element of FIG. 1; and FIG. 7 is a side elevational view of the control rod or stent for the dissector element.

DESCRIPTION OF THE PREFERRED EMBODIMENTS

Referring to FIG. 1, there is shown a perspective view of a preferred embodiment of the blunt dissector device of the present invention. The device, which is generally denoted 10, basically comprises a handle portion 12, a control portion 14 and a finger-like dissector portion 16. As will appear, these designations are more or less arbitrary since, for example, the handle portion performs a control function, and are provided here for ease of description.

The handle portion 12 includes a pair of scissor elements 18 and 20 comprising a pair of elongate legs 18a and 20a terminating at one end on finger grips 18b and 20b and which are pivotably connected together at an intermediate location along the lengths thereof at a pivot element 22. A spring 24 disposed between and connected to the legs 18a and 20a distally of pivot element biases apart the finger grips or loops 18a and 20a while a locking or latching mechanism, denoted 26, is used to lock the scissor legs in position against the biasing force of spring 24.

The locking mechanism 26 comprises, in the illustrated embodiment, a pair of locking members 28 and 30 disposed on the respective legs 18a and 18b. Locking member 28 includes a projecting tongue or latch 28a, a portion of which is visible in FIG. 1 and which is adapted to engage in one of a series of laterally spaced grooves 30a formed in locking member 30. It will be appreciated that the pivoting position, i.e., the amount of pivoting, of the scissor elements 18 and 20 is controlled by the groove 30a selected and that this position is releasably locked or latched when tongue or latch 28a is inserted into a selected groove 30a, as shown in FIG. 2. It will also be understood that the locking or latching mechanism 26 can take other forms and that, in general, any locking device or mechanism that will retain the scissor elements 18 and 20 in a selected position can be used.

The control portion 14 of device 10 includes a circular plate member or plate 32 disposed at the other end of scissor element 18 from finger loop or grip 18b. Plate 32 includes a semicircular aperture 34 therein as well as a central opening 36. A control member (rod) or stent 38 including a finger control knob 38a extends through aperture 34 and provides control of the movement of dissector portion 16, as described below. Further, a cannula or channel element 40 extends through central opening 36 and along the dissector portion 16 to permit the insertion of various instruments required in specific procedures as well as the insertion of a light guide or fiber optic element to enable viewing of the operation site, as is also described below.

Control rod or stent 38 is best seen in FIG. 7 and, as illustrated, includes, in addition to control knob 38a, a non-flexible portion 38' and a flexible portion 38".

Handle or scissor element 20 terminates at the end thereof opposite to finger grip or loop 20b in a cylindrical or barrel member 42 having central cylindrical opening 42a therethrough (see FIG. 4). Barrel member 42 is offset from the plate 32 and receives the proximal non-flexible end of the dissector portion 16. As illustrated in, e.g., FIGS. 3 and 4, the control rod or stent 38 and the cannula or channel element 40 extend through respective openings 38b and 40a in dissector portion 16. Unless locked in place as described below, the dissector portion is freely rotatable within barrel 42 under the control of control rod or stent 38, between the limits defined by semicircular slot or aperture 34. It will be appreciated that instead of being integral with scissor element 20, barrel 42 could be formed by a separate element releasably secured to scissor element 20 by a cylindrical spring or the like fitted around the circumference of barrel 42.

As is best seen in FIGS. 3 and 4, the proximal, non-flexible end section 16a of dissector portion 16 includes a circumferential groove 44 therein which enables a set screw 46 received in an threaded bore or aperture 48 in barrel 42 to engage in groove 44 and thus hold end section 16a in place. In this way the angular position of the dissector portion 16 can be fixed as desired, between the limits defined by semicircular slot 34.

Dissector portion 16 includes, in addition to non-flexible end section 16a, a series of further dissector elements 16b, 16c, 16d, 16e and 16f of like shape and distal or terminating element 16g which has the general shape of the end of a human finger and which includes a recess 50 in the upper (as viewed in FIGS. 1 and 2) surface thereof. Elements 16a to 16g are hinged together and, as an example, element 16b hinged to the non-flexible section 16a by a hinge arrangement 52 perhaps best seen in FIG. 5 and FIG. 6 (which is partially broken away to show this). Hinge arrangement 52 includes a tongue 54 extending from element 16a into a slot or groove 56 in section 16b and held in place by a pin 58. Similar hinge arrangements corresponding to hinge 52 and including tongues 54 and pins 58 are used to connect the remaining elements together.

The tapered shapes provided by the angled end faces of elements 16b to 16f (perhaps best seen in FIGS. 1, 2 and 5), and the hinging together of the elements described above, enable the elements to pivot about the respective hinges 52 and thus curl or bend away from the straight line or axial position shown in FIG. 1 to the curved position shown in solid lines in FIG. 2 wherein the flexible part of dissector element 16 is curved or curled upwardly. This movement is controlled by control rod or stent 38 and more particularly, by handle portion 12. Specifically, by closing handle 12, i.e., by bringing finger grips or loops 18b and 20b closer together, plate 32 pivots away from barrel 42 and thus causes the fixed end of the flexible portion of control rod 38 to exert a force on the distal end element 16g of dissector portion 16, and to also cause, in the orientation of control rod 38 that is illustrated, elements 16b to 16g to pivot in the same vertical plane to produce the curling or bending effect described above and illustrated in FIG. 2.

It will be appreciated that the amount of curvature of the flexible section of dissector portion 16 can be controlled by controlling the amount of closure or squeezing together of scissor elements 18a and 20a. Moreover, in accordance with an important feature of the invention, the desired curvature can be "locked in" by virtue of the action of locking mechanism 26 described above.

It will also be understood that, in accordance with a further important feature of the invention, by rotating knob 38a, and thus control rod 38, within the semicircular aperture 34, dissector 16 can also be caused to rotate. Accordingly, if the knob 38a is moved to the endmost portion on the left (as viewed in FIGS. 1 and 2) defined by aperture 34, the flexible portion of dissector element 16 is caused to curl or bend to the left in a horizontal plane containing the fixed portion 16a, as indicated in dashed lines in FIG. 2, and if knob 38a is moved to the right endmost position, the dissector element 16 is caused to bend the to the right in the same plane, as is also indicated in dashed lines. As discussed above, the angular position of the dissector element 16 can be fixed using set screw 46 which can be screwed into threaded bore 48 to engage in groove 44 in the proximal end of fixed dissector portion 16a and hence inhibit further rotation of the dissector element 16. Again, intermediate angular positions can, of course, be selected as well, depending on the amount of rotation of control rod 38 and thus of dissector 16.

As illustrated in FIG. 3 but is not shown in the other figures, an outer covering or cuff 60, made of silicone or a like material, is used to cover the non-flexible and flexible parts of the dissector element 16 to create a smooth surface and to eliminate or reduce abdominal insufflation in use of the dissector device 10.

It will be appreciated from the foregoing that flexing of the flexible part of dissector 16 (elements 16b to 16g) can be carried out without any rotation of the handle portion 12, i.e., with handle portion 12 held stationary. Thus, the handles 18 and 20 can be held by the surgeon in a comfortable position when the dissector portion 16 is rotated so as to direct the tip to the desired angle for dissection. Dissection of the anatomical tissue is achieved by suitable flexing (and unflexing) of the flexible part of dissector element 16 through the action of the scissor-like handles 18 and 20, when unlocked. This action is assisted by spring 24 which makes this movement very simple. Although the length of the flexible part of dissector element 16 can be made longer or shorter to fit the dissection required with a particular procedure or operation, an exemplary length of the flexible part of dissector 16 is about 9 to 10 cm. Advantageously, the length can vary from 2 to 5 or more centimeters.

As discussed above, the dissector of the invention serves to reduce the possibility of unintended perforation of dissected organs such as can occur with prior art devices and procedures and to assist in this, the diameter of the dissector is made relatively large as compared with dissectors presently in use. In accordance with a specific non-limiting example, the diameter of the dissector is on the order of 10 mm. Of course, the diameter of the dissector can be increased if the procedure to be undertaken demands this whereas, on the other hand, the diameter can also be decreased depending on the procedure. However, with a small diameter (e.g., less than about 7 mm.) some of the features of the larger diameter embodiments may have to be eliminated. For example, the cannula or channel tube 40 provided in the center of the dissector 16 may have to be dispensed with because of size considerations. In general, the diameter of the dissector element 16 is on the order of 5mm to 12 or more mm.

As briefly discussed above, the channel tube 40 can be used to insert a fiber-optic light element, a specifically designed small diameter video camera or various instruments needed for dissection such as scissors, cautering devices, "grasps" and the like. The end of channel tube 40 is caused to puncture the outer cuff 60 at the distal end to permit this to be done.

The opening 40b as depicted in FIG. 6 at the tip or distal end of the dissector 16 can be used to enable placement of ("hucking" in) the conventional device or drain that is placed around the dissected organ for traction or side manipulation.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A blunt dissector device comprising:

an elongate dissector element including a flexible distal end portion comprising a plurality of separate, rigid, pivotable dissector members disposed in serial relation, and pivotable connector means for pivotably connecting adjacent dissector members together; and control means, including a control rod extending along said dissector element and including a relatively flexible distal portion disposed within said distal end portion of said dissector element, for exerting a force on said dissector element so as to cause controlled pivoting of aid dissector elements to thereby produce a desired curvature of said flexible distal end portion for dissection, said control means including locking means for maintaining said force on said dissector element so as to rigidly maintain said flexible distal end portion in the desired curvature.

2. A blunt dissector device as claimed in claim 1, wherein said elongate dissector element further includes a substantially non-flexible proximal end portion and said control means further includes mounting means for mounting said proximal end portion of said dissector element and means for effecting angular rotation of said proximal end portion of said dissector element within said mounting means so as to cause rotation of said dissector element without movement of said mounting means.

3. A blunt dissector device as claimed in claim 1, wherein said dissector element further comprises a resilient outer covering presenting a smooth surface.

4. A blunt dissector device as claimed in claim 1, wherein said control means includes a pair of pivotable control arms, one of said control arms being connected to said control rod to control movement thereof.

5. A blunt dissector device as claimed in claim 4, wherein said control arms include scissor-type gripping loops at the distal ends thereof.

6. A blunt dissector device as claimed in claim 5, wherein said control means further comprises a spring means for biasing said gripping loops away from each other.

7. A blunt dissector device as claimed in claim 4, wherein said one control arm includes a plate member having a curved slot therein defining end points, and wherein said control rod extends through said curved slot and includes a control means at the proximal end thereof for enabling movement of said control rod within said slot to thereby selectively control angular movement of the dissector element between said end points.

8. A blunt dissector device as claimed in claim 7, wherein said curved slot comprises a semicircular slot.

9. A blunt dissector device as claimed in claim 7, further comprising securing means for releasably securing said dissector element in a desired angular position.

10. A blunt dissector device as claimed in claim 9, wherein said control means includes a mounting means for mounting the proximal end of said dissector element, said securing means comprising a circumferential groove in the outer surface of said dissector element at the proximal end thereof, and a set screw, disposed in said mounting means, for, in use, engaging in said groove to fix the angular position of said dissector element.

11. A blunt dissector device as claimed in claim 7, wherein said dissector element includes a non-pivotable dissector member and said plurality of pivotable dissector members, said relatively non-flexible portion of said control rod extending through said non-pivotable dissector member and said relatively flexible portion of said control rod extending through said pivotable dissector members and being connected to the most distal pivotable dissector member.

12. A blunt dissector device as claimed in claim 11, further comprising a tubular member extending along the length of said dissector element and terminating at said most distal dissector member for permitting the insertion of auxiliary implements through said dissector element.

13. A device as claimed in claim 1, wherein said connector means includes a pin connector defining a pivot axis for adjacent dissector members.

14. A blunt dissector device comprising:

an elongate blunt dissector element including a proximal end portion and a movable flexible distal end portion having a tip, said flexible end portion comprising a plurality of separate, rigid, pivotable dissector members disposed in serial relation, and pivotable connector means for pivotably connecting adjacent dissector members together;

control means connected to said dissector element for controlling movement of said flexible distal end portion of said dissector element so as to enable selective movement thereof from a first position wherein the distal end portion is coaxial with the proximal end portion into a rigid, curved configuration wherein the distal end portion forms a curved finger-like dissector; and mounting means for rotatably mounting the proximal end portion of said dissector element so as to enable said dissector element to be rotated relative to said mounting means so as to control positioning of the tip of said dissector element.

15. A blunt dissector device as claimed in claim 14 wherein said control means includes locking means for maintaining the desired curvature of said flexible distal end portion.

16. A blunt dissector device as claimed in claim 15, wherein said control means includes a control rod extending along said dissector element and comprising a first relatively non-flexible proximal portion disposed with the proximal end portion of said dissector element and second, relatively flexible distal portion disposed within said distal end portion of said dissector element, said proximal end portion of said dissector element being substantially non-flexible and said control means further comprising manually operated means connected to said control rod for effecting angular rotation of said proximal end portion of said dissector element within said mounting means so as to cause rotation of dissector element without movement of said mounting means.

17. A blunt dissector device as claimed in claim 16, wherein said control means includes a pair of pivotable control arms pivotably connected together intermediate the ends thereof, one end of one of said control arms being connected to said control rod to control movement thereof and one end of the other of said control arms being connected to said mounting means.

18. A blunt dissector device as claimed in claim 17, wherein said control arms include gripping loops at the other, distal ends thereof, and said device further comprises a spring means for biasing said gripping loops away from each other.

19. A blunt dissector device as claimed in claim 18, wherein said one control arm includes at said one end thereof a plate member having a curved slot therein defining end points and said control rod extends through said curved slot and includes said manually operated means at the proximal end thereof for enabling control of movement of said control rod within said slot to thereby selectively control angular movement of the dissector element between said end points.

20. A device as claimed in claim 14, wherein said connector means includes a pin connector defining a pivot axis for adjacent dissector members.

21. A blunt dissector device comprising:

an elongate blunt dissector element including a substantially non-flexible proximal end portion and a flexible distal end portion;

mounting means for rotatably mounting said proximal end portion of said dissector element; and control means, including a control rod extending along said dissector element and comprising a first relatively non-flexible proximal portion disposed within the proximal end portion of said dissector element and second, relatively flexible distal portion disposed within said distal end portion of said dissector element, for exerting a force on said dissector element so as to produce a desired curvature of said flexible distal end portion, said control means including locking means for maintaining said force on said dissector element so as to maintain the desired curvature of said flexible distal end portion and manually operated means connected to said control rod for effecting angular rotation of said proximal end portion of said dissector element within said mounting means so as to cause rotation of dissector element without requiring movement of said mounting means, said dissector element including a non-pivotable dissector member, a plurality of separate pivotable dissector members arranged in serial relation and connector means, including a pin connector defining a pivot axis, for pivotably connecting adjacent dissector members together to enable pivoting thereof relative to one another, said relatively non-flexible portion of said control rod extending through said non-pivotable dissector member and said relatively flexible portion of said control rod extending through said pivotable dissector members and being connected to the most distal pivotable dissector member.

22. A blunt dissector device comprising:

an elongate dissector element including a flexible distal end portion; and control means, including a control rod extending along said dissector element and comprising a first relatively non-flexible proximal portion and second, relatively flexible distal portion disposed within said distal end portion of said dissector element, for exerting a force on said dissector element so as to produce a desired curvature of said flexible distal end portion, said control means including locking means for maintaining said force on said dissector element so as to maintain the desired curvature of said flexible distal end portion, said control means further including a pair of pivotable control arms pivotably connected together intermediate the ends thereof, one end of one of said control arms being connected to said control rod and one end of the other of said control arms being connected to said mounting means.

\* \* \* \* \*